United States Patent
Ho et al.

(10) Patent No.: US 8,263,570 B2
(45) Date of Patent: Sep. 11, 2012

(54) TREATING PICORNAVIRUS INFECTION BY TARGETING MICRORNA MIR-141

(75) Inventors: Bing-Ching Ho, Chiayi (TW); Sung-Liang Yu, Taipei (TW); Pan-Chyr Yang, Taipei (TW); Chun-Nan Lee, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/638,737

(22) Filed: Dec. 15, 2009

(65) Prior Publication Data

US 2010/0160414 A1    Jun. 24, 2010

Related U.S. Application Data

(60) Provisional application No. 61/122,530, filed on Dec. 15, 2008.

(51) Int. Cl.
*A61K 48/00* (2006.01)

(52) U.S. Cl. ...... 514/44; 536/24.5; 536/24.31; 536/24.1

(58) Field of Classification Search ........................ None
See application file for complete search history.

(56) References Cited

U.S. PATENT DOCUMENTS

2005/0261218 A1* 11/2005 Esau et al. ...................... 514/44

FOREIGN PATENT DOCUMENTS

| WO | WO2006-128245 | | 12/2006 |
| WO | WO2007090073 | * | 8/2007 |

OTHER PUBLICATIONS

Iorio et al. Cancer Rese 2007 (67) 18: pp. 8699-8707.*
Oberste et al. J. of Virology 1999, p. 1941-1948.*
Nielson (Gene Therapy 2005 (12), 956-957.*
David T. Humphrey et al.; "MicroRNAs control translation initiation by inhibiting eukaryotic initiation factor 4E_cap and poly(A) tail function"; PNAS 102(47):16961-16966 (2005).
Anne Saumet et al.; "Anti-viral RNA silencing: do we look like plants"; Retrovirology 3:3; 2006.

* cited by examiner

*Primary Examiner* — Kimberly Chong
(74) *Attorney, Agent, or Firm* — Birch, Stewart, Kolasch & Birch, LLP

(57) ABSTRACT

Treatment of picornavirus infection by inhibiting miR-141 activity. Also disclosed herein are a method for identify miR-141 inhibitory compounds and a method for identifying a target viral infection to be treated by anti-miR-141 therapy.

13 Claims, 3 Drawing Sheets

Fig. 1

```
3'-GGUAGAAAUGG-UCUGUCACAA-5'  hsa-miR-141
   ||||   ||   ||||||||||
5'-CCATTCATATTAAGACAGTGTA-3'  eIF4E-3'UTR
```

A.

B.

A.

B.

TREATING PICORNAVIRUS INFECTION BY TARGETING MICRORNA MIR-141

RELATED APPLICATION

This application claims priority to U.S. Provisional Application No. 61/122,530, filed on Dec. 15, 2008, the content of which is hereby incorporated by reference in its entirety.

BACKGROUND OF THE INVENTION

MicroRNAs are short single-strand RNA molecules that regulate gene expression post transcriptionally via RNA interference. In general, they bind to the 3' untranslated regions (3' UTRs) of their target mRNAs, thereby blocking translation. Certain viruses carry genes encoding microRNAs. These viral microRNAs regulate both viral and cellular gene expression to facilitate their proliferation in host cells.

Picornavirus is a group of small, non-enveloped viruses containing positive-strand RNAs coated by icosahedral protein shells. It causes a wide range of illnesses in both humans and animals, e.g., aseptic meningitis, encephalitis, the common cold, hand-foot-and-mouth disease, conjunctivitis, herpangina, and hepatitis. No medications are currently available for treating picornavirus infections.

SUMMARY OF THE INVENTION

In one aspect, the present invention features a method of treating piconavirus infection or reducing viral protein production by administering to a subject in need of the treatment an effective amount of a microRNA miR-141 inhibitory agent, optionally combined with another anti-viral drug. This inhibitor agent is either an antisense oligonucleotide of miR-141 or an interfering RNA targeting transcription factor early growth response 1 (EGR1). An antisense oligonucleotide of miR-141 can be a RNA including a nucleotide sequence at least 90% identical to a nucleotide sequence complementary to miR-141. Preferably, the antisense RNA includes the nucleotide sequence of CCAUCUUUACCAGACAGUG UUA (SEQ ID NO:1). An EGR1-targeting small interfering RNAs (siRNA) is a RNA specifically binding to a suitable region within the EGR1 mRNA (e.g., Region 1, 2, or 3), thereby inhibiting EGR1 translation via RNA interference. Examples of EGR1-targeting siRNA include, but are not limited to, siEGR1-1 (5'-AAAGGUUGCUGUCAUGUCCga; SEQ ID NO:2), siEGR1-2 (5'-AAUGGGACUGCUGUCG-UUga; SEQ ID NO:3), and siEGR1-3 (5'-UUAGGGUAG-UUGUCCAUGGug; SEQ ID NO:4).

The subject to be treated in the method of this invention can be a human patient infected with an enterovirus (e.g., enterovirus 71), a poliovirus (e.g., poliovirus 3), or a coxsackievirus (e.g., coxsackievirus B3).

In another aspect, this invention features an isolated nucleic acid containing a nucleotide sequence at least 90% identical to SEQ ID NO:1 or the sequence complementary to EGR1 Region 1, E2 Region 2, or EGR1 Region 3. Examples of the isolated nucleic acid include SEQ ID NOs:1-4. The term "isolated nucleic acid" used herein refers to a nucleic acid substantially free from naturally associated molecules, i.e., the naturally associated molecules constituting at most 20% by dry weight of a preparation containing the polypeptide. Purity can be measured by any appropriate method, e.g., column chromatography, polyacrylamide gel electrophoresis, and HPLC.

Also within the scope of this invention is use of any of the miR-141 inhibitory agent mentioned above in manufacturing a medicament for treating picornavirus infection or reducing viral protein production.

In yet another aspect, this invention features a method for identifying an anti-picornavirus drug candidate. This method includes at least four steps: (i) providing cells infected with a picornavirus, the cells exhibiting a lower level of eIF-4E as compared to non-infected cells; (ii) contacting the cells with a compound; (iii) examining the activity of miR-141 in the cells; and (iv) assessing whether the compound is a drug candidate for treating infection caused by the picornarivus. If the compound decreases miR-141 activity, it is identified as the anti-picornavirus drug candidate. In one example, the activity of miR-141 is determined by the amount of this miRNA. In another example, it is determined by the expression level of a miR-141 target gene (e.g., eIF-4E).

The present invention also features a method of identifying a target viral infection (i.e., an infection caused by a target virus) that can be treated by anti-miR-141 therapy. This method includes (i) providing cells infected with a virus, (ii) examining in the cells the activity of miR-141 (i.e., the amount of miR-141 or the expression level of its target gene); and (iii) determining whether the infection caused by the virus is a target viral infection to be treated in anti-miR-141 therapy. A post-infection increase in the miR-141 amount or a post-infection decrease in the expression level of its target gene indicates that the infection is the target viral infection.

The details of one or more embodiments of the invention are set forth in the description below. Other features or advantages of the present invention will be apparent from the following drawing and detailed description of the example, and also from the appended claims.

BRIEF DESCRIPTION OF THE DRAWING

The drawing is first described.

FIG. 1 is a diagram showing the base pairs formed between hsa-miR-141 (SEQ ID NO:5) and the 3' UTR (SEQ ID NO:6) of the eukaryotic initiation factor 4E (eIF-4E) gene.

DETAILED DESCRIPTION OF THE INVENTION

Figure 2:
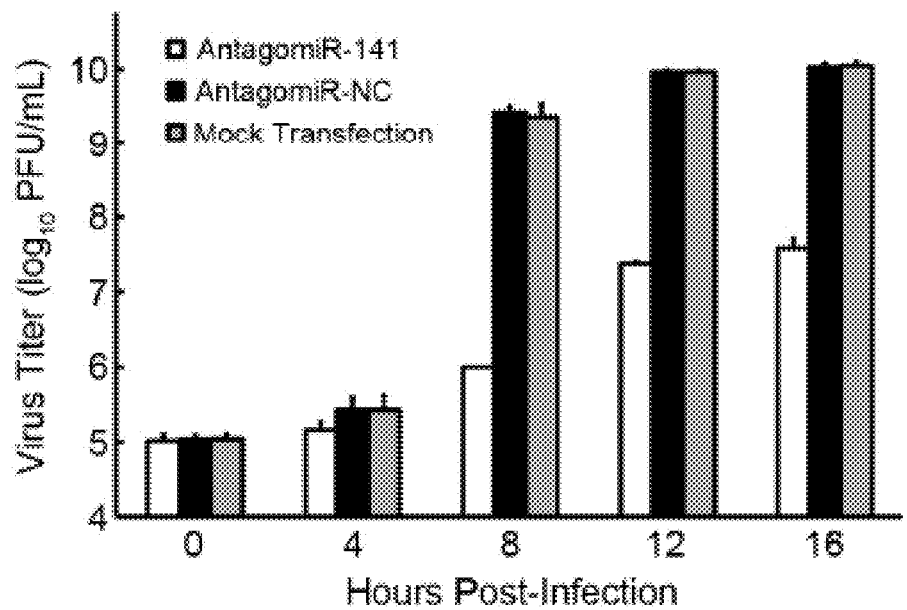
FIG. 2 is a chart showing inhibitory effects of antigomiR-141 on viral proliferation. Panel A: inhibition of EV71 viral proliferation by antigomiR-141 in human rhabdomyosarcoma cells. Panel B: inhibition of EV71 viral proliferation by antigomiR-141 in human globlastoma SF-268 cells.
Figure 2:
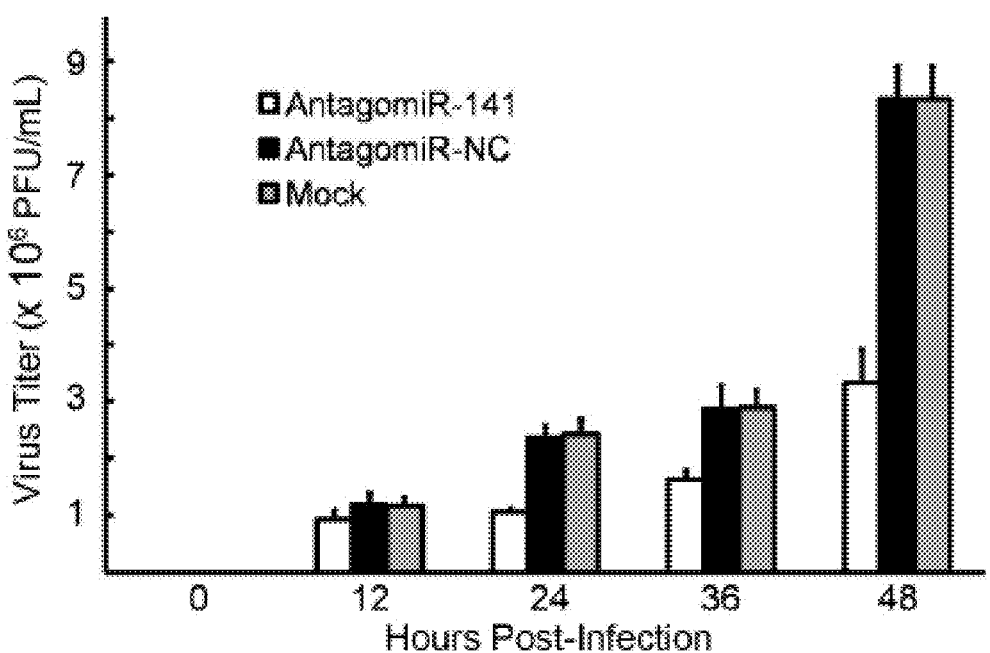

Applicants have discovered that certain picornaviruses (e.g., enterovirus 71, poliovirus 3, and coxsackievirus B3) unexpectedly up-regulate expression of miR-141 in human cells. The nucleotide sequences of human miR-141, including precursor miRNA, mature miRNA, and antisense miRNA star, can be found under GenBank Accession Number NR_029682 (29 Oct. 2009). Human miR-141 base pairs with the 3' UTR of human eIF-4E mRNA (see FIG. 1) and silences its translation via RNA interference. As eIF-4E is essential in cellular protein synthesis, picornavirus-induced miR-141 over-expression results in suppression of cellular protein synthesis. Applicants have also discovered that this viral-induced protein synthesis suppression was rescued by inhibiting miR-141 activity by blocking the binding between miR-141 and eIF-4E 3'UTR or by reducing the expression level of miR-141.

Accordingly, the present invention relates to a method of treating picornavirus infection using an effective amount of a miR-141 inhibitory agent. Picornavirus includes, but are not limited to, enterovirus (e.g., human enterovirus A, B, C, or D, poliovirus, and coxsackievirus), Rhinovirus (e.g., human rhinovirus A, B, or C), Hepatovirus (also known as Heparnavirus, such as Hepatitis A virus), Cardiovirus (e.g., Encephalomyocarditis virus), Aphthovirus (e.g., Foot-and-mouth disease virus). The term "treating" as used herein refers to the application or administration of a composition including one or more active agents to a subject infected with a picornavirus with the purpose to cure, heal, alleviate, relieve, alter, remedy, ameliorate, improve, or affect the infection, or the symptoms of the infection. "An effective amount" as used herein refers to the amount of each active agent required to confer therapeutic effect on the subject, either alone or in combination with one or more other active agents. Effective amounts vary, as recognized by those skilled in the art, depending on route of administration, excipient choice, and co-usage with other active agents.

The miR-141 inhibitory agent used in methods of this invention can be an antisense oligonucleotide of miR-141, i.e., an oligomer of ribonucleic acid, an oligomer of deoxyribonucleic acid, or a mimetic thereof that is complementary or partially complementary to a fragment of precursor miR-141 (e.g., mature miR-141 or miR-141*; see GenBank Accession Number NR_029682). Such an antisense oligonucleotide, preferably 15 to 50-nucleotide (e.g., 19-25-nt) in length, includes a sequence at least 80% (e.g., 90%, 95%, or 98%) identical to the sequence complementary to the just-mentioned fragment in miR-141. It forms base pairs with that fragment and blocks the binding between miR-141 and eIF-4E mRNA or processing of precursor miR-141 to mature miR-141.

The miR-141 inhibitory agent can also be an interfering RNA that targets transcription factor EGR1 ("EGR1 interfering RNA"), which regulates miR-141 expression. The coding sequence (SEQ ID NO:7) of this protein is shown below:

atggccgcggccaaggccgagatgcagctgatgtccccgctgcagatctc tgacccgttcggatcctttcctcactcgcccaccatggacaactaccta
(Region 1)

agctggaggagatgatgctgctgagcaacggggctcccagttcctcggc gccgccggggccccagagggcagcggcagcaacagcagcagcagcagcag cggggcggtggaggcggcgggggcggcagcaacagcagcagcagcagca gcaccttcaaccctcaggcggacacgggcgagcagccctacgagcacctg accgcagagtcttttcctgacatctctctgaacaacgagaaggtgctggt ggagaccagttaccccagccaaaccactcgactgcccccatcacctata ctggccgcttttccctggagcctgcacccaacagtggcaacaccttgtgg cccgagccctcttcagcttggtcagtggcctagtgagcatgaccaaccc accggcctcctcgtcctcagcaccatctccagcggcctcctccgcctccg cctcccagagcccaccoctgagctgcgcagtgccatccaacgacagcagt
(Region 2)

cccatttactcagcggcacccaccttccccacgccgaacactgacatttt ccctgagccacaaagccaggccttcccgggctcggcagggacagcgctcc agtacccgcctcctgcctaccctgccgccaagggtggcttccaggttccc atgatccccgactacctgtttccacagcagcagggggatctgggcctggg cacccagaccagaagcccttccagggcctggagagccgcacccagcagc cttcgctaacccctctgtctactattaaggcctttgccactcagtcgggc tcccaggacctgaaggccctcaataccagctaccagtcccagctcatcaa acccagccgcatgcgcaagtacccccaaccggcccagcaagacgccccccc acgaacgcccttacgcttgcccagtggagtcctgtgatcgccgcttctcc cgctccgacgagctcacccgccacatccgcatccacacaggccagaagcc cttccagtgccgcatctgcatgcgcaacttcagccgcagcgaccacctca ccacccacatccgcacccacacaggcgaaaagcccttcgcctgcgacatc tgtggaagaaagtttgccaggagcgatgaacgcaagaggcataccaagat ccacttgcggcagaaggacaagaaagcagacaaaagtgttgtggcctctt cggccacctcctctctctcttcctacccgtccccggttgctacctcttac ccgtccccggttactacctcttatccatcccccggccaccacctcatccc atcccctgtgcccacctcctttctcctctcccggctcctcgacctacccat cccctgtgcacagtggcttccctccccgtcggtggccaccacgtactcc tctgttcccctgctttcccggcccaggtcagcagcttcccttcctcagc tgtcaccaactccttcagcgcctccacagggctttggacatgacagcaa**
(Region 3)

cctttt**ctcccaggacaattgaaatttgctaa

An interfering RNA is a RNA molecule (e.g., miRNA or siRNA) that inhibits expression of a target gene via RNA interference. RNA interference is a process in which a double-strand RNA directs homologous sequence-specific degradation of messenger RNA. In mammalian cells, RNAi can be triggered by 21-nucleotide duplexes of siRNA without activating the host interferon response.

The EGR1 interfering RNA mentioned above can target a suitable region within the EGR1 mRNA, preferably within its coding region (e.g., Regions 1-3 highlighted in SEQ ID NO:7 above). The interfering RNA can include a nucleotide sequence at least 80% (e.g., 90%, 95%, or 98%) identical to the complementary sequence of the target region and forms base-pairs under physiological conditions.

The "percent identity" of two nucleic acids is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215: 403-10, 1990. BLAST nucleotide searches can be performed with the NBLAST program, score=100, wordlength-12 to obtain nucleotide sequences homologous to the nucleic acid molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Both the antisense oligonucleotide and the interfering RNA used in the method of this invention can be prepared by conventional methods, i.e., chemical synthesis or recombinant technology. Preferably, it is composed of non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the antisense oligonucleotide or interfering RNA has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the antisense oligonucleotide or interfering RNA used in this invention includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the antisense oligonucleotide or interfering RNA includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyladenine, 5-propynyluracil and 5-propynylcytosine). See Sanghvi, et al., eds., Antisense Research and Applications, CRC Press, Boca Raton, 1993, pp. 276-278).

When an antisense oligonucleotide of miR-141 is prepared, its ability to block the binding between miR-141 and the 3' UTR of the eIF-4E mRNA can be verified by methods known in the art. Below is an example. The 3' UTR of the eIF-4E mRNA is amplified by polymerase chain reaction (PCR) and the PCR product is linked to a reporter gene (e.g., a luciferase gene), downstream of its coding region. The reporter gene carrying the eIF-4E 3' UTR, cloned into an expression vector, is then introduced into a host cell suitable for expression of the reporter gene. The host cell is further transfected with miR-141 either alone or together with the antisense oligonucleotide to be tested. After culturing under suitable conditions, the host cell is examined for the expression level of the reporter gene. If the antisense oligonucleotide rescues the inhibition of the reporter gene expression induced by miR-141, it indicates that this oligonucleotide is capable of blocking miR-141 from base pairing with the 3' UTR of the eIF-4E mRNA.

The activity of an EGR1 interfering RNA also can be examined via conventional methods. See, e.g., Example 3 below.

The antisense oligonucleotide of miR-141 or the EGR1 interfering RNA can be mixed with a pharmaceutically acceptable carrier to form a pharmaceutical composition. An "acceptable carrier" is a carrier compatible with the active ingredient of the composition (and preferably, stabilizes the active ingredient) and not deleterious to the subject to be treated. Suitable carriers include, but are not limited to, (a) salts formed with cations (e.g., sodium, potassium, ammonium, magnesium, calcium) and polyamines (e.g., spermine and spermidine); (b) acid addition salts formed with inorganic acids (e.g., hydrochloric acid, hydrobromic acid, sulfuric acid, phosphoric acid, nitric acid); (c) salts formed with organic acids (e.g., acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid); and (d) salts formed from elemental anions (e.g., chlorine, bromine, and iodine). Other suitable carriers include microcrystalline cellulose, mannitol, glucose, defatted milk powder, polyvinylpyrrolidone, starch, and a combination thereof.

Conventional methods, known to those of ordinary skill in the art of medicine, can be used to administer to a subject the pharmaceutical composition described above. For example, the pharmaceutical composition described above can be delivered topically (e.g., via ophthalmic, vaginal, and rectal administration), pulmonarily (e.g., via inhalation or insufflation of powders or aerosols), intratracheally, intranasally, transdermally, orally, or parenterally. Parenteral administration includes intravenous, intraarterial, subcutaneous, intraperitoneal or intramuscular injection or infusion; or intracranial administration (e.g., intrathecal or intraventricular). When oral administration is applied, it is preferred that the antisense oligonucleotide includes at least one 2'-O-methoxyethyl modification.

An injectable composition containing the antisense oligonucleotide of miR-141 may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, the oligonucleotide can be administered by the drip method, whereby a pharmaceutical formulation containing the oligonucleotide and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of a peptide, can be dissolved and administered in a pharmaceutical excipient such as sterile water, 0.9% saline, or 5% glucose solution.

To facilitate delivery, the antisense oligonucleotide or interfering RNA can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antisense oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

To improve efficacy, the pharmaceutical composition described above can be co-used with another antiviral agent.

Also disclosed herein is a method for identifying a potential anti-picornavirus drug. In this method, cells infected with a picornavirus are treated with a compound under suitable conditions and then examined for cellular miR-141 activity. Such a compound can be either a small molecule or a macromolecule (e.g., nucleic acid and protein). If the compound inhibits miR-141 activity, it is identified to be a potential anti-picornavirus drug. miR-141 activity can be determined by examining the amount of miR-141 per se in the treated cells via a conventional method, e.g., real-time PCR. It also can be determined by examining the expression level (i.e., the message RNA level or protein level) of one of its target genes. The table below lists a number of exemplary target genes that are regulated by miR-141:

TABLE 1

Target Genes of miR-141

| Gene | RefSeq ID | Description | GO Terms |
| --- | --- | --- | --- |
| JAG1 | NM_000214 | Jagged-1 precursor (Jagged1) (hJ1) (CD339 antigen). | regulation of cell migration, angiogenesis, growth factor activity, Notch binding, cell fate determination, regulation of cell proliferation, cell communication, Notch signaling pathway, extracellular region, myoblast differentiation, structural molecule activity, neurogenesis, development, integral to plasma membrane, endothelial cell differentiation, hemopoiesis, membrane, keratinocyte differentiation, calcium ion binding |
| ATXN1 | NM_000332 | Ataxin-1 (Spinocerebellar ataxia type 1 protein). | RNA binding, nucleus, cytoplasm |
| PAFAH1B1 | NM_000430 | Platelet-activating factor acetylhydrolase IB alpha subunit (PAF acetylhydrolase 45 kDa subunit) (PAF-AH 45 kDa subunit) (PAF-AH alpha) (PAFAH alpha) (Lissencephaly-1 protein) (LIS-1). | cell differentiation, microtubule-based process, microtubule associated complex, cell cortex, cell motility, neurogenesis, kinetochore, cell division, astral microtubule, establishment of mitotic spindle orientation, nuclear membrane, signal transduction, mitosis, dynein binding, cytoskeleton, microtubule, cell cycle, lipid metabolism |

TABLE 1-continued

Target Genes of miR-141

| Gene | RefSeq ID | Description | GO Terms |
| --- | --- | --- | --- |
| UBE3A | NM_000462<br>NM_130839<br>NM_130838 | Ubiquitin-protein ligase E3A (EC 6.3.2.-) (E6AP ubiquitin-protein ligase) (Oncogenic protein-associated protein E6-AP) (Human papillomavirus E6-associated protein). | proteolysis and peptidolysis, ubiquitin-protein ligase activity, brain development, ubiquitin conjugating enzyme activity, nucleus, intracellular, ubiquitin-dependent protein catabolism, ligase activity, ubiquitin cycle |
| EIF4E | NM_001968 | Eukaryotic translation initiation factor 4E (eIF4E) (eIF-4E) (mRNA cap-binding protein) (eIF-4F 25 kDa subunit). | protein binding, translational initiation, eukaryotic translation initiation factor 4F complex, RNA cap binding, regulation of translation, translation initiation factor activity |
| KPNA3 | NM_002267 | Importin alpha-3 subunit (Karyopherin alpha-3 subunit) (SRP1-gamma). | intracellular protein transport, protein transporter activity, protein binding, nucleus, binding, protein complex assembly, nuclear pore, nuclear localization sequence binding, NLS-bearing substrate-nucleus import |
| PLAG1 | NM_002655 | pleiomorphic adenoma gene 1 | transcription factor activity, nucleus, zinc ion binding, metal ion binding, nucleic acid binding |
| SP3 | NM_003111<br>NM_001017371 | Transcription factor Sp3 (SPR-2). | transcriptional repressor activity, regulation of transcription, DNA-dependent, DNA binding, transcription, protein binding, transcriptional activator activity, nucleus, zinc ion binding, nucleic acid binding, metal ion binding |
| FKBP5 | NM_004117 | FK506-binding protein 5 (EC 5.2.1.8) (Peptidyl-prolyl cis-trans isomerase) (PPIase) (Rotamase) (51 kDa FK506-binding protein) (FKBP-51) (54 kDa progesterone receptor-associated immunophilin) (FKBP54) (P54) (FF1 antigen) (HSP90-binding immunophilin) | protein folding, unfolded protein binding, isomerase activity, FK506 binding, peptidyl-prolyl cis-trans isomerase activity, binding, nucleus |
| KCNA2 | NM_004974 | Potassium voltage-gated channel subfamily A member 2 (Voltage-gated potassium channel subunit Kv1.2) (HBK5) (NGK1) (HUKIV). | potassium ion transport, cation transport, voltage-gated potassium channel activity, protein binding, delayed rectifier potassium channel activity, integral to membrane, voltage-gated potassium channel complex, potassium ion binding, cation channel activity, membrane |
| FCHSD2 | NM_014824 | FCH and double SH3 domains 2 | |
| TM9SF4 | NM_014742 | Transmembrane 9 superfamily protein member 4. | transport, integral to membrane, transporter activity, membrane |
| SFPQ | NM_005066 | Splicing factor, proline- and glutamine-rich (Polypyrimidine tract- binding protein-associated splicing factor) (PTB-associated splicing factor) (PSF) (DNA-binding p52/p100 complex, 100 kDa subunit) (100-kDa DNA-pairing protein) (hPOMp100). | regulation of transcription, DNA-dependent, DNA binding, transcription, nucleotide binding, DNA repair, protein binding, nuclear mRNA splicing, via spliceosome, RNA binding, nucleus, RNA splicing, DNA recombination |
| HOXA11 | NM_005523 | Homeobox protein Hox-A11 (Hox-11).<br>[Source: Uniprot/SWISSPROT; Acc: P31270] | transcription factor activity, nucleus, regulation of transcription, DNA-dependent, morphogenesis |
| JARID1B | NM_006618 | Jumonji, AT rich interactive domain 1B (RBP2-like) | transcriptional repressor activity, protein binding, nucleus, negative regulation of transcription, DNA-dependent, regulation of transcription, DNA-dependent, DNA binding, zinc ion binding |
| SCN3A | NM_006922 | Sodium channel protein type III alpha subunit (Voltage-gated sodium channel alpha subunit Nav1.3) (Sodium channel protein, brain III alpha subunit) (Voltage-gated sodium channel subtype III). | cation transport, voltage-gated sodium channel activity, integral to membrane, sodium ion transport, cation channel activity, membrane, calcium ion binding, voltage-gated sodium channel complex |
| WBP4 | NM_007187 | WW domain-binding protein 4 (WBP-4) (Formin-binding protein 21). | nuclear mRNA splicing, via spliceosome, spliceosome complex, zinc ion binding, metal ion binding, nucleic acid binding |
| TM9SF4 | NM_014742 | Transmembrane 9 superfamily protein member 4. | transport, integral to membrane, transporter activity, membrane |

TABLE 1-continued

Target Genes of miR-141

| Gene | RefSeq ID | Description | GO Terms |
| --- | --- | --- | --- |
| ZFHX1B | NM_014795 | Zinc finger homeobox protein 1b (Smad-interacting protein 1) (SMADIP1). | transcriptional repressor activity, regulation of transcription, DNA-dependent, SMAD binding, transcription factor activity, neurogenesis, nucleus, negative regulation of transcription, zinc ion binding, nucleic acid binding, phosphatase regulator activity, metal ion binding |
| DNAJC13 | NM_015268 | DnaJ homolog subfamily C member 13 (Required for receptor-mediated endocytosis 8). | protein folding, unfolded protein binding, heat shock protein binding, binding |
| THRAP2 | NM_015335 | Thyroid hormone receptor-associated protein 2 (Thyroid hormone receptor-associated protein complex 240 kDa component-like). | nucleus, regulation of transcription, DNA-dependent, receptor activity, transcription |
| SYT4 | NM_020783 | Synaptotagmin-4 (Synaptotagmin IV) (SytIV). | transport, synapse, integral to membrane, synaptic vesicle, synaptic vesicle transport, transporter activity, membrane, regulation of calcium ion-dependent exocytosis, calcium ion binding |
| WTAP | NM_152857 NM_004906 NM_152858 | Wilms' tumor 1-associating protein (WT 1-associated protein) (Putative pre-mRNA-splicing regulator female-lethal(2D) homolog). | nucleus |
| CPEB4 | NM_030627 | cytoplasmic polyadenylation element binding protein 4 | nucleotide binding, nucleic acid binding |
| CPEB2 | NM_182646 NM_182485 | cytoplasmic polyadenylation element binding protein 2 isoform A | nucleotide binding, nucleic acid binding |
| NARG1 | NM_057175 | NMDA receptor-regulated protein 1 (N-terminal acetyltransferase) (Tubedown-1 protein) (Tbdn100) (Gastric cancer antigen Ga19). | cell differentiation, acetyltransferase activity, angiogenesis, ribosome binding, N-terminal protein amino acid acetylation, transcription, cytoplasm, protein binding, positive regulation of transcription, DNA-dependent, transcription factor complex, nucleus |
| AEBP2 | NM_153207 | AE binding protein 2 | nucleus, zinc ion binding, metal ion binding, nucleic acid binding |

Other genes regulated by miR-141 can be identified by a computational target gene prediction program, e.g., Target-Combo described in Sethupathy et al., Nat. Methods 3:881-886 (2006). See also diana.pcbi.upenn.edu/cgi-bin/Target-Combo.cgi.

The present invention also provides a method for identifying a virus that up-regulates the miR-141 activity in its host cells. Infection caused by such a virus can be treated in an anti-miR-141 therapy, i.e., via suppressing miR-141 activity or expression. Suppression of miR-141 activity includes down-regulating the level of miR-141 or blocking its binding to a target message RNA. The just-mentioned method can be performed by examining in cells infected with a virus the level of miR-141 or the expression level of a miR-141 target gene (see Table 1 above). If the infected cells exhibit an elevated level of miR-141 or a decreased expression level of the target gene, it indicates that the infection caused by that virus can be treated in anti-miR-141 therapy.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Example 1

Viral Infection-Induced miR-141 Overexpression Suppressed Cellular eIF-4E Expression Human rhabdomyosarcoma (RD) cells were cultured in MEM medium supplemented with 1 mM L-glutamate, 100 units/mL penicillin, 100 µg/mL streptomycin, and 10% fetal bovine serum (Gibco). The cells were infected with poliovirus type 3 (PV3), coxsackievirus B3 (CVB3), or enterovirus 71 (EV71) in a serum-free medium and the cytopathic effect caused by viral infection was photographed under ZEISS Axiovert 200M (Zeiss) with 50× magnification. The captured photographs were analyzed using ImageXpress$^{MICRO}$ and MetaXpress image analysis software (MDS Analytical Technologies). Mock-infected cells were used as a control in this study.

After infection, the cells were harvested and RNAs were extracted from both viral-infected and mock-infected cells using the Trizol reagent (Invitrogen). Real-time PCR analysis was performed to determine the levels of miR-141 and eIF-4E mRNA in these cells by the TaqMan gene expression assay (000463 and Hs00908915; Applied Biosystems) according to the manufacturer's instructions. See Belsham et al., *Trends Microbiol* 8:330-335 (2000). The threshold cycle (Ct) is defined as the fraction cycle number at which the fluorescence exceeds 0.2, the fixed threshold. Total RNA input was normalized based on the Ct values of U6 snRNA (an internal control) determined by the same assay the TaqMan assay. The fold change was calculated by the formula $2^{-\Delta CT} \times K$, where $-\Delta CT = -[CT_{miRNA} - CT_{U6\ snRNA}]$ and K is a constant.

The results obtained from this study indicate that, 8 hours after infection, the levels of miR-141 in EV71-infected cells, PV3-infected cells, and B3-infected cells were 16-fold, 14-fold, and 31 fold greater than that in control cells, respectively. Further, the mRNA levels of eIF-4E were found to decrease in a time-dependent manner in viral-infected cells but not in the control cells.

The following luciferase assay was performed to confirm the inhibitory effect of miR-141 on eIF-4E expression. The full-length 3'UTR (wtUTR, containing the target site of miR-141) was amplified from the genomic DNA of RD cells by primers F1 (5'-gagctcGAAGACACCTTCTGAGTATTCT-3'; SEQ ID NO:8) and R1 (5'-gccggcTAAAAGACAATTCACT-GTACACAT-3; SEQ ID NO:9). Two mutated 3'UTR fragments (mutUTRs) were obtained via PCR using primers F1 and mutR1 (5'-TTTTGTAGTGAGTCTTAATATGAAT-3; SEQ ID NO:10) and primers mutF1 (5'-ATTCATATTAA-GACTCACTACAAAA-3; SEQ ID NO:11) and R1. Both the wild-type 3' UTR and the mutated 3' UTRs were cloned into the pMIR-reporter luciferase vector (Ambion) to obtain luciferase-wtUTR and luciferase-mutUTR reporter constructs.

$1 \times 10^4$ HEK293T cells were seeded in a well of a 96-well plate 24 h prior to transfection. Each of the luciferase reporter constructs, or control plasmid pRL-TK (Promega), was co-introduced into the cells with miR-141 at a ratio of 5:1, using the RNAi-fect reagent (Qiagen). 48 hours after the transfection, the Dual-Glo luciferase substrate (Promega) was added to each well and the luminescent signals were determined by Victor$^3$ multilabel counter (PerkinElmer) following the manufacturer's instructions. The activity of *Renilla* luciferase was used as an internal control to normalize transfection efficiency. All transfections were carried out in triplicate in 96-well plates.

The results obtained from this study show that miR-141 inhibited luciferase activity by up to 50% in cells co-transfected with the luciferase-wtUTR reporter construct but not in cells co-transfected with the luciferase-mutUTR report constructs. This demonstrate that miR-141 suppresses eIF-4E expression via base-pairing with its 3'UTR.

The full-length eIF4E coding sequence was amplified from RD cells via RT-PCR, ligated, at its 5' end, with a sequence coding for the V5 tag, and, at its 3' end, with either wtUTR or a mutUTR. The resultant ligation products were cloned into the pcDNA 3.1 expression vector (Invitrogen) to produce expression constructs V5-eIF4E-wtUTR and V5-eIF4E-mutUTR. These two expression constructs were introduced into RD cells and stable cell lines were established via neomycin selection.

The stable cell lines thus obtained were transfected with miR-141 and the expression of V5-eIF4E was examined by Westernblot as follows, using an anti-V5 antibody. The cells were harvested and lyzed in RIPA lysis buffer (50 mM Tris-HCl (pH 7.4), 150 mM NaCl, 1 mM EDTA, 1% Triton X-100, 0.1% SDS, 1% sodium deoxycholate, 1 mM PMSF, and a protease inhibitor cocktail) and the protein concentration in the cell lysate was measured by the BCA protein assay (Bio-Rad). Proteins were resolved by 12.5% sodium dodecyl sulfate polyacrylmide gel electrophoresis and transferred to a PVDF membrane. After being blocked with 5% skimmed milk in Tris-buffered saline (TBS) (20 mM Tris-HCl (pH 7.5), 150 mM NaCl, 0.5% Tween-20), the membrane was incubated with a primary antibody specific to β-actin (1:5000; Sigma), which served as an internal control, or a primary antibody specific to the V5 tag (1:5000; Invitrogen). The membrane was then washed for several times, incubated with a dye-conjugated secondary antibody, and subjected to color development. The Westernblot data indicates that miR-141 negatively regulated V5-eIF4E expression in cells transfected with the V5-eIF4E-wtUTR construct in a dose-dependent manner. The inhibitory effect of miR-141 was not observed in cells transfected with the V5-eIF4E-mutUTR construct and miR-141. These results confirm that miR-141 negatively regulates eIF4E translation via interacting with the 3' UTR of its mRNA.

Next, the stable cell lines mentioned above were infected with EV71, CVB3, or PV3 at an m.o.i. 10 to examine whether the virus could inhibit eIF4E expression by inducing miR-141 expression. The cells were collected 4, 8, and 12 hours after infection and cellular proteins were subjected to Westernblot analysis as described above. The results demonstrate that infection with EV71, CVB3, or PV3 reduced the levels of V5-eIF4E in the cells transfected with the V5-eIF4E-wtUTR construct in a time-dependent manner, but not in the cells transfected with the V5-eIF4E-mutUTR construct. Clearly, these picornaviruses reduce the levels of eIF4E in infected cells via induction of miR-141 expression, thereby suppressing production of host cell proteins. Thus, inhibiting miR-141 activity can rescue the suppression of host cell protein production caused by picornavirus infection.

Example 2

Inhibition of Viral Proliferation by AntagomiR-141

Human RD cells were cultured in MEM medium supplemented with 1 mM L-glutamate, 100 units/mL penicillin, 100 μg/mL streptomycin, and 10% fetal bovine serum (Gibco). These cells were transfected with antagomiR-141 (CCAU-CUUUACCAGACA GUGUUA; SEQ ID NO:1), an RNA complementary to miR-141, or a negative control RNA by siPORT NeoFX transfection reagent (Ambion), following the manufacturer's instructions. The transfected RD cells, as well as mock-transfected RD cells, were infected with EV71 in a serum-free medium. The cytopathic effect induced by EV71 infection was photographed using ZEISS Axiovert 200M (Zeiss) with 50× magnification. The captured photographs were analyzed using ImageXpress$^{MICRO}$ and MetaXpress image analysis software (MDS Analytical Technologies). The built-in integrated morphometry analysis function of MetaXpress was used to quantify the cytopathic effect. Numeric data were analyzed using MS Excel (Microsoft). Results obtained in this study indicate that antigomiR-141 significantly attenuated EV71 induced cytopathic effect in RD cells as compared with either the negative control RNA.

The mock-transfected, negative control-transfected, and antagomiR-141-transfected RD cells were examined for levels of cellular protein synthesis at different time points after EV71 infection by a metabolic labeling assay. Briefly, 4, 8, 12, or 16 hr after EV71 infection, the RD cells were cultured in methionine-free DMEM medium (Invitrogen) supplemented with 2 mM L-glutamine for 20 minutes. 20 μCi/mL [$^{35}$S] methionine (NEN) was added to the medium to label de novo synthesized proteins. Fifteen minutes later, the cells were harvested and the labeled proteins were analyzed by 12% SDS-PAGE. In mock-transfected and negative control-transfected RD cells, cellular protein synthesis was suppressed 4 hr after EV71 infection. Surprisingly, the level of this suppression was significantly reduced in RD cells transfected with antagomiR-141, indicating that antagomiR-141 rescued EV71-induced suppression of cellular protein synthesis.

The levels of viral proteins, i.e., capsid proteins VP1 and VP3, in the RD cells mentioned above were examined by Westernblot. Briefly, RD cells were harvested and suspended in RIPA lysis buffer (50 mM Tris-HCl (pH 7.4), 150 mM NaCl, 1 mM EDTA, 1% Triton X-100, 0.1% SDS, 1% sodium deoxycholate, 1 mM PMSF, protease inhibitor cocktail). The protein concentrations of the lysates were measured by the BCA protein assay (BioRad). Proteins contained in the lysates were resolved by sodium dodecyl sulfate polyacrylmide gel electrophoresis (12.5%) and transferred to a nitrocellulose membrane. The membrane was blocked with 5% skimmed milk in Tris-buffered saline (20 mM Tris-HCl (pH 7.5), 150 mM NaCl, 0.5% Tween-20), washed, and then incubated with primary antibodies specific to 0 actin (1:5000; Sigma), VP1 (1:2000; Chemicon), and VP3 (1:2000; Chemicon). After being washed for several times, the membrane was incubated with HPR-conjugated anti-mouse IgG antibody (1:5000; Santa Cruz). Results thus obtained showed that levels of VP1 and VP3 in antagomiR-141-transfected RD cells were significantly lower than those in mock-transfected or negative control-transfected RD cells. These data demonstrate that antatomiR-141 reduced viral protein production.

Finally, the viral titers in the EV71-infected RD cells were determined as follows. RD cells were seeded in a 6-well plate and infected with 100 µL per well of diluted viral stocks. An hour later, the infected cells were washed, suspended in a fresh medium, and placed on top of a medium plate containing 0.3% agar. After being cultured for three days, the cells were fixed with formaldehyde and stained with crystal violet to allow formation of plaques. The number of the plaques represents viral titer. The results indicate that antagomiR-141 reduced the EV71 viral titer by about 1,000 fold as compared to the negative control RNA. See FIG. 2, Panel A.

The inhibitory effect of antagomiR-141 on viral proliferation was also examined in neural cells as follows. Human glioblastoma SF-268 cells were cultured in RPMI-1640 medium supplemented with 1 mM L-glutamate, 100 units/mL penicillin, 100 µg/mL streptomycin, and 10% fetal bovine serum (Gibco). The SF-268 cells were transfected with antagomiR-141 or the negative control RNA by siPORT NeoFX transfection reagent (Ambion), following the manufacturer's instructions. The transfected cells and mock-transfected control cells were infected with EV71 in a serum-free medium. The cytopathic effect induced by EV71 infection was examined following the method described above. The levels of cellular eIF4E at various time points after infection (i.e., 8, 16, 24, 32, 40, 48, and 56) were examined by Westernblot The results indicate that EV71 infection resulted in reduced levels of the endogenous eIF4E over time and the reduction of eIF4E was rescued by antigomiR-141, but not the control RNA.

The viral titers in the EV71-infected SF-268 cells were determined by the conventional plaque formation assay. As shown in FIG. 2, Panel B, antagomiR-141 reduced EV71 proliferation 24 hours after infection and the reduction level peaked at 48 hours post infection.

Example 3

Inhibition of Viral Proliferation by Small Interfering RNAs Targeting EGR1

EGR1 was identified as a transcription factor regulating miR-141 expression. The levels of mRNA and protein of EGR1 were examined by real-time PCR and Westernblot, respectively, in RD cells infected with EV71. The results show that both mRNA and protein levels of EGR1 were increased up to 100 fold 4 and 8 hours after infection relative to those in mock-infected cells. This indicates that viral infection induces expression of EGR1 and consequently up-regulates miR-141.

Two potential EGR1 binding sites were identified in the 5' regulatory region of the miR-141 gene. A chromatin immunopredipitation assay was performed, following the protocol provided by Updated Biotechnology, to examine whether EGR1 directly binds to the two putative binding sites. A DNA fragment encoding EGR1 with a V5 tag was inserted into pcDNA 3.1 and introduced into RD cells. 48 hours after transfection, the cells were treated with 1% formaldehyde for 10 min at 37° C. and washed twice in ice-cold phosphate-buffered saline containing protease inhibitors (1 mM PMSF, 1 µg/ml aprotinin, and 1 µg/ml pepstatin A). The cells were pelleted and lysed in SDS Lysis Buffer (Upstate Biotechnology) and the lysate samples thus obtained were sonicated to shear DNA to lengths between 200 and 1000 bp. An aliquot of the sheared DNA was analyzed by agarose gel electrophoresis to examine the length and amount of the sheared DNA. The sheared DNA was incubated overnight at 4° C. with mouse anti-V5 monoclonal antibody (Invitrogen). Immune complexes were captured by Sepharose beads coated with salmon sperm DNA-bovine serum albumin and treated with DNase- and RNase-free proteinase K, extracted with phenol and chloroform, and then precipitated. The DNA pellet was collected and subjected to PCR analysis, using primers flanking the two putative EGR1 binding sites mentioned above. The results show that both EGR1 binding sites were amplified in the just-mentioned PCR analysis, indicating that these two sites bound to EGR1-V5.

The levels of miR-141 and eIF4E were also examined in the RD cells transfected with the pcDNA-EGR1-V5 construct by real-time PCR and Westernblot analysis. The date thus obtained indicate that in cells expressing EGR1-V5, the level of miR-141 was significantly higher than that in the control cells (mock-infected cells or vector-transfected cells) and the level of eIF4E was significantly lower than that in the control cells.

In sum, the above results demonstrate that EV71 infection up-regulated expression of EGR1, which in turn induced miR-141 expression and decreased the level of eIF4E, thereby inhibiting cellular protein synthesis in infected cells.

Next, an RNA interference analysis was conducted to study whether suppressing EGR1 expression could inhibit viral proliferation. siEGR1-1, siEGR1-2, and siEGR1-3, three siRNAs targeting EGR1 having the nucleotide sequences of 5'-AAAGGUUGCU GUCAUGUCCga (SEQ ID NO:2), 5'-AAUGGGACUGCUGUCGUUga (SEQ ID NO:3), and 5'-UUAGGGUAGUUGUCCAUGGug (SEQ ID NO:4), respectively, were introduced into RD cells by Lipofectamine 2000 reagent (Invitrogen) and, 24 hours later, the transfected RD cells were infected with EV71 virus. The supernatants of the cell cultures were collected 4 or 8 hours post infection and analyzed by the plaque assay described above to determine viral titers. The cells were also collected; total RNAs were extracted from the cells and analyzed by SYBR Green real-time PCR (Applied Biosystems) to determine the EGR1 expression levels.

Figure 3:
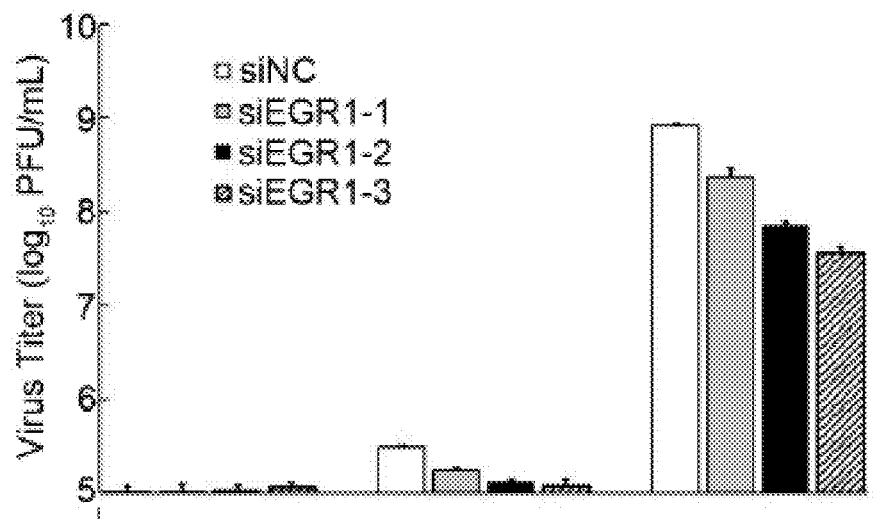
FIG. 3 is a chart showing inhibitory effects of three small interference RNAs (siEGR1-1, siEGR1-2, and siEGR1-3) that target transcription factor early growth response 1 (EGR1). Panel A: inhibition of EV71 viral proliferation by siEGR1-1, siEGR1-2, and siEGR1-3 in human rhabdomyosarcoma cells. Panel B: reduction of EGR1 levels by siEGR1-1, siEGR1-2, and siEGR1-3 in human rhabdomyosarcoma cells infected with EV71.
Figure 3:
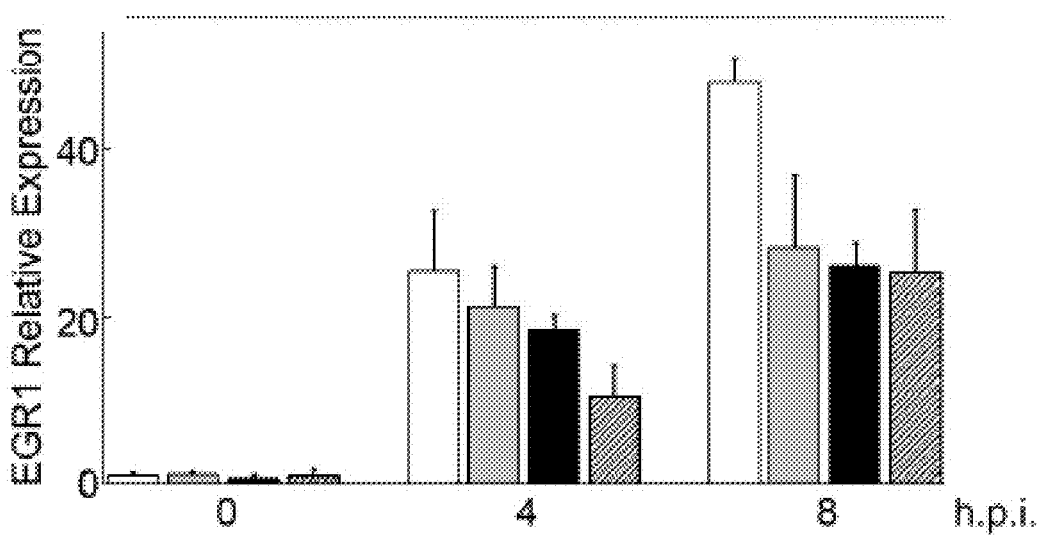

As shown in FIG. 3, all of siEGR1-1, siEGR1-2, and siEGR1-3 reduced the EGR1 levels in EV71-infected RD cells 4 hours after infection and the reduction level peaked 8 hours post infection. These siRNAs also reduced viral titers in the supernatants by 3 to 20 folds 4 or 8 hours after infection relative to a control RNA. No production of interferon alpha was observed in cells transfected with the three EGR1-targeting siRNAs and the control RNA in an ELISA assay. Sequence alignment analysis indicated that none of siEGR1-1, siEGR1-2, and siEGR1-3 targets the EV71 genome.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating infection caused by an enterovirus, comprising:
    administering to a subject infected with an enterovirus an antisense oligonucleotide of human miR-141 in an amount effective to treat said infection in the subject, wherein the enterovirus is selected from the group consisting of enterovirus 71 (EV71), coxsackievirus B3 (CVB3) and poliovirus type 3 (PV3).

2. The method of claim 1, wherein the antisense oligonucleotide is an antisense RNA.

3. The method of claim 2, wherein the antisense RNA includes a nucleotide sequence at least 90% identical to a nucleotide sequence complementary to human miR-141.

4. The method of claim 3, wherein the antisense RNA includes the nucleotide sequence CCAUCUUUACCAGACAGUGUUA (SEQ ID NO:1).

5. A method of reducing viral protein production, comprising
    administering to a subject infected with an enterovirus an antisense oligonucleotide of human miR-141 in an amount effective to reduce viral protein production in the subject, wherein the enterovirus is selected from the group consisting of enterovirus 71 (EV71), coxsackievirus B3 (CVB3) and poliovirus type 3 (PV3).

6. The method of claim 5, wherein the antisense oligonucleotide is an antisense RNA of human miR-141 including the nucleotide sequence of SEQ ID NO:1.

7. The method of claim 1, wherein the enterovirus is enterovirus 71.

8. The method of claim 5, wherein the enterovirus is enterovirus 71.

9. A method for inhibiting viral proliferation or reducing viral protein production in a cell infected with an enterovirus, comprising in vitro treating the cell with an effective amount of an antisense oligonucleotide of miR-141, wherein the enterovirus is selected from the group consisting of enterovirus 71 (EV71), coxsackievirus B3 (CVB3) and poliovirus type 3 (PV3).

10. The method of claim 9, wherein the antisense oligonucleotide is an antisense RNA.

11. The method of claim 10, wherein the antisense RNA includes a nucleotide sequence at least 90% identical to a nucleotide sequence complementary to miR-141.

12. The method of claim 11, wherein the antisense RNA includes the nucleotide sequence CCAUCUUUACCAGACAGUGUUA (SEQ ID NO:1).

13. The method of claim 9, wherein the enterovirus is enterovirus 71.

* * * * *

```
                        SEQUENCE LISTING

<160> NUMBER OF SEQ ID NOS: 11

<210> SEQ ID NO 1
<211> LENGTH: 22
<212> TYPE: RNA
<213> ORGANISM: Artificial Sequence
<220> FEATURE:
<223> OTHER INFORMATION: Oligonucleotide

<400> SEQUENCE: 1
ccaucuuuac cagacagugu ua                                            22

<210> SEQ ID NO 2
<211> LENGTH: 21
<212> TYPE: RNA
<213> ORGANISM: Artificial Sequence
<220> FEATURE:
<223> OTHER INFORMATION: Oligonucleotide

<400> SEQUENCE: 2
aaagguugcu gucauguccg a                                             21

<210> SEQ ID NO 3
<211> LENGTH: 20
<212> TYPE: RNA
<213> ORGANISM: Artificial Sequence
<220> FEATURE:
<223> OTHER INFORMATION: Oligonucleotide

<400> SEQUENCE: 3
aaugggacug cugucguuga                                               20

<210> SEQ ID NO 4
<211> LENGTH: 21
<212> TYPE: RNA
<213> ORGANISM: Artificial Sequence
<220> FEATURE:
<223> OTHER INFORMATION: Oligonucleotide

<400> SEQUENCE: 4
uuaggguagu uguccauggu g                                             21

<210> SEQ ID NO 5
<211> LENGTH: 21
<212> TYPE: RNA
<213> ORGANISM: Artificial Sequence
<220> FEATURE:
<223> OTHER INFORMATION: Oligonucleotide

<400> SEQUENCE: 5
gguagaaaug gucugucaca a                                             21

<210> SEQ ID NO 6
<211> LENGTH: 22
```

```
<212> TYPE: DNA
<213> ORGANISM: Artificial Sequence
<220> FEATURE:
<223> OTHER INFORMATION: Oligonucleotide

<400> SEQUENCE: 6
ccattcatat taagacagtg ta                                              22

<210> SEQ ID NO 7
<211> LENGTH: 1632
<212> TYPE: DNA
<213> ORGANISM: Homo sapiens

<400> SEQUENCE: 7
atggccgcgg ccaaggccga gatgcagctg atgtccccgc tgcagatctc tgacccgttc      60 ggatccttc ctcactcgcc caccatggac aactacccta agctggagga gatgatgctg      120
ctgagcaacg gggctcccca gttcctcggc gccgccgggg ccccagaggg cagcggcagc      180
aacagcagca gcagcagcag cggggggcggt ggaggcgggg ggggcggcag caacagcagc      240
agcagcagca gcaccttcaa ccctcaggcg gacacgggcg agcagcccta cgagcacctg      300
accgcagagt cttttcctga catctctctg aacaacgaga aggtgctggt ggagaccagt      360
taccccagcc aaaccactcg actgccccc atcacctata ctggccgctt ttccctggag      420
cctgcaccca cagtggcaa caccttgtgg cccgagcccc tcttcagctt ggtcagtggc      480
ctagtgagca tgaccaaccc accggcctcc tcgtcctcag caccatctcc agcggcctcc      540
tccgcctccg cctcccagag cccacccctg agctgcgcag tgccatccaa cgacagcagt      600
cccatttact cagcggcacc caccttcccc acgccgaaca ctgacatttt ccctgagcca      660
caaagccagg ccttccccggg ctcggcaggg acagcgctcc agtacccgcc tcctgcctac      720
cctgccgcca agggtggctt ccaggttccc atgatccccg actacctgtt tccacagcag      780 caggggggatc tgggcctggg caccccagac cagaagccct tccagggcct ggagagccgc      840
acccagcagc cttcgctaac ccctctgtct actattaagg cctttgccac tcagtcgggc      900
tcccaggacc tgaaggccct caataccagc taccagtccc agctcatcaa cccagccgc      960 atgcgcaagt accccaaccg gccagcaag acgcccccc acgaacgccc ttacgcttgc     1020
ccagtggagt cctgtgatcg ccgcttctcc cgctccgacg agctcacccg ccacatccgc     1080
atccacacag gccagaagcc cttccagtgc cgcatctgca tgcgcaactt cagccgcagc     1140
gaccacctca ccacccacat ccgcacccac acaggcgaaa agcccttcgc ctgcgacatc     1200
tgtggaagaa agtttgccag gagcgatgaa cgcaagaggc ataccaagat ccacttgcgg     1260
cagaaggaca agaaagcaga caaaaagtgtt gtggcctctt cggccacctc ctctctctct     1320
tcctacccgt ccccggttgc tacctcttac ccgtcccgg ttactacctc ttatccatcc     1380
ccggccacca cctcatacc ccatccctgtg cccacctcct tctcctctcc cggctcctcg     1440 acctaccat ccctgtgca cagtggcttc ccctccccgt cggtggccac cacgtactcc     1500
tctgttcccc ctgctttccc ggcccaggtc agcagcttcc cttcctcagc tgtcaccaac     1560
tccttcagcg cctccacagg gctttcggac atgacagcaa cctttttctcc caggacaatt     1620 gaaattgct aa                                                         1632

<210> SEQ ID NO 8
<211> LENGTH: 28
<212> TYPE: DNA
<213> ORGANISM: Artificial Sequence
<220> FEATURE:
<223> OTHER INFORMATION: Oligonucleotide
```

```
<400> SEQUENCE: 8
gagctcgaag acaccttctg agtattct                                          28

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9
gccggctaaa agacaattca ctgtacacat                                        30

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
ttttgtagtg agtcttaata tgaat                                             25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide

<400> SEQUENCE: 11
attcatatta agactcacta caaaa                                             25
```